(12) United States Patent
Jones et al.

(10) Patent No.: US 9,000,275 B2
(45) Date of Patent: Apr. 7, 2015

(54) COMPOSITIONS AND METHODS FOR ASSAYING MARKERS TIGHTLY LINKED TO RESISTANCE LOCUS BS2 OF PEPPER

(75) Inventors: Carl Martin Jones, Davis, CA (US); Diane Kerr Avner, Vacaville, CA (US)

(73) Assignee: Monsanto Technology LLC, St. Louis, MO (US)

( * ) Notice: Subject to any disclaimer, the term of this patent is extended or adjusted under 35 U.S.C. 154(b) by 1416 days.

(21) Appl. No.: 12/546,406

(22) Filed: Aug. 24, 2009

(65) Prior Publication Data

US 2010/0083399 A1    Apr. 1, 2010

Related U.S. Application Data

(60) Provisional application No. 61/093,011, filed on Aug. 29, 2008.

(51) Int. Cl.
| | |
|---|---|
| *A01H 1/04* | (2006.01) |
| *C12Q 1/68* | (2006.01) |
| *A01H 5/00* | (2006.01) |
| *A01H 5/08* | (2006.01) |
| *A01H 5/10* | (2006.01) |

(52) U.S. Cl.
CPC ............... *C12Q 1/6895* (2013.01); *A01H 1/04* (2013.01); *A01H 5/08* (2013.01)

(58) Field of Classification Search
None
See application file for complete search history.

(56) References Cited

U.S. PATENT DOCUMENTS

| | | | |
|---|---|---|---|
| 6,262,343 B1 | 7/2001 | Staskawicz et al. | 800/279 |
| 6,762,285 B2 | 7/2004 | Staskawicz et al. | 530/372 |
| 8,013,222 B2 * | 9/2011 | McCarthy | 800/317.1 |

OTHER PUBLICATIONS

Tai et al (Theor Appl Genet 99: 1201-1206, 1999, cited in the IDS filed Jan. 22, 2010).*
Kousik et al (Plant Disease 82(2): 181-186, 1998).*
Hibberd et al. Phytopathology 77: 1304-1307 (1987).*
Agarwal et al. Plant Cell Reports 27: 617-631 (2008).*
Minsavage et al. Molecular Plant-Microbe Interactions 3(1): 41-47 (1990).*
Bosland, P.W. Vegetable Cultivar Descriptions for Northern America, Pepper (A-L), from online cuke.hort.ncsu.edu/cucurbit/wehner/vegcult/pepperal.html (available 2014).*
Gassmann et al., "Molecular evolution of virulence in natural field strains of *Xanthomonas campestris* pv. *vesicatoria*," *J. of Bacteriology*, 182(24):7053-7059, 2000.
GenBank Accession No. AY702979, dated Nov. 16, 2006.
Jordan et al., "Physical delimination of the pepper Bs3 resistance gene specifying recognition of the AvrBs3 protein from *Xanthomonas campestris* pv. *vesicatoria*," *Theor. Appl. Genet.*, 113:895-905, 2006.
Kousik et al., "Development of bacterial spot on near-isogenic lines of bell pepper carrying gene pyramids composed of defeated major resistance genes," *Phytopathology*, 89(11):1066-1072, 1999.
Mudgett et al., "Molecular signals required for type III secretion and translocation of the *Xanthomonas campestris* AvrBs2 protein to pepper plants," *PNAS*, 97(21):13324-13329, 2000.
Park et al., "Molecular marker-assisted selection of the Bs2 bacterial spot resistance gene in diverse pepper cultivatars and breeding lines," *HortSci.*, 42(4):1006, 2007.
Pernezny et al., "Host-plant resistance and management of bacterial spot of pepper," Florida Cooperative Extension of Bacterial Service, Institute of Food and Agricultural Sciences, University of Florida, June 2008.
Pierre et al., "High-resolution genetic mapping of the pepper resistance locus Bs3 governing recognition of the *Xanthomonas campestris* pv *vesicatoria* AvrBs3 protein," *Theor. Appl. Genet.*, 101:255-263, 2000.
Rommens et al., "Exploiting the full potential of disease-resistance genes for agricultural use," *Curr. Opin. Biotechnology*, 11(2):120-125, 2000.
Stall et al., "Durability of resistance in tomato and pepper to xanthomonads causing bacterial spot," *Ann. Rev. of Phytopathology*, 47:265-284, 2009.
Tai et al., "Expression of the Bs2 pepper gene confers resistance to bacterial spot disease in tomato," *PNAS*, 96(24):14153-14158, 1999.
Tai et al., "High-resolution genetic and physical mapping of the region containing the Bs2 resistance gene of pepper," *Theor. Appl. Genet.*, 99:1201-1206, 1999.
Yang et al., "Mining tomato genome sequence databases for molecular markers: application to bacterial resistance and marker assisted selection," *Acta Hort.*, 695:241-250, 2005.

* cited by examiner

*Primary Examiner* — David T Fox
(74) *Attorney, Agent, or Firm* — Dentons US LLP; Matthew L. Madsen Esq.

(57) ABSTRACT

The invention relates to compositions and methods for genotypically screening pepper lines for the presence of a polymorphism at the Bs2_5859 locus genetically linked to the Bs2 gene conferring resistance to Bacterial Spot caused by *Xanthomonas campestris*. Further provided are methods for producing plants displaying Bs2-mediated resistance, and fruit and seeds therefrom.

31 Claims, 8 Drawing Sheets

FIG. 1

Race Classification of *Xanthomonas campestris* pv. *vesicatoria* Strains Pathogenic on Pepper

| X.c.v. Pepper Race | Pepper Differential Lines — Functional resistance gene(s) in pepper plant | | | | |
|---|---|---|---|---|---|
| | ECW (No R gene) | ECW 10R ($BS_1$ gene) | ECW 20R ($BS_2$ gene) | ECW 30R ($BS_3$ gene) | ECW123 ($BS_1$, $BS_2$, $BS_3$ genes) |
| 0 | S | HR | HR | HR | HR |
| 1 | S | S | HR | HR | HR |
| 2 | S | HR | HR | S | HR |
| 3 | S | S | HR | S | HR |
| 4 | S | S | S | HR | HR |
| 5 | S | HR | S | S | HR |
| 6 | S | S | S | S | S |
| 7 | S | S | HR | HR | HR |
| 8 | S | S | HR | S | HR |
| 9 | S | S | S | HR | HR |
| 10 | S | S | S | S | S |

ECW = Early Cal Wonder
ECW 10R, ECW 20R, and ECW 30R are near isogenic lines and differ solely in the presence of the $BS_1$, $BS_2$, and $BS_3$ genes, respectively
ECW123 harbors $BS_1$, $BS_2$, and $BS_3$ resistance genes
ECW12346 harbors $BS_1$, $BS_2$, $BS_3$, $bs_5$, and $bs_6$ resistance genes S = Susceptible reaction to *Xanthomonas campestris* pv. *vesicatoria*
HR = Hypersensitive-resistant reaction to *Xanthomonas campestris* pv. *vesicatoria*
R = Resistant (non-hypersensitive) reaction to *Xanthomonas campestris* pv. *Vesicatoria*

Note: Hypersensitive resistance is dominant to susceptibility

Characterization of YAC sequence targeted regions for marker identification

- Bs2 exons
- Sequence duplications
- Repetitive elements
- Regions targeted for marker development

FIG. 5

```
31081 gctaagacca ccaagtcatt caaacaattc aagaggatgt gcatatcgaa attcatgaaa
31141 acttgtgcaa agattctctc ttgcaattca caaacatgtc gtggtcaagt atcttgtaac
31201 aaaccatgca actctctaaa atcatcacct ctcatttata taaacaagaa aacaccctct
31261 cttcacttca taaccaaaat caagtcttaa ataatagtaa agacattgat atcatgcttc
31321 tcaaatatgca aattgaatat ttcataacct atgaaaacaa gatgctttat aacaagagag
31381 ggttatatat gttcatgctc tcaattcaat cattcaaact caaacgcatg tatacttaca
31441 tacgagtacg aatcaaattt aggggaaagc ctcaagacca aaatattata tcattgaaag
31501 agttcacact gcatgctttt taatgaaatt caagaaccct tcgtaaaaat atgattctc
31561 gacattcaaa atatatttaa aatgattta ccatgcccat gtagtttagg aaaacccaac
31621 gtacttaga ttacttggtt cgaagaatag aattcgaatc ttgactcgtc tcttggaaat
31681 cttgaactta aagatggatt ctgatcttt tgggagggaa cttgatgtat aaagacgttt
31741 taatcttccg ttttcactac ttgggaccat ggaaaaaaga tgagactgcc cctcaacttt
31801 ttaaaaaatt actgcagaat ctccttttg gagctcactg cgacgcagtg acatgctcat
31861 tgccataccc accgcgacac ggtgtaatcg cggtgagtta ttgaaacttg accactgtcg
31921 atttgaattt caccgagacg cgacagaggc tccatcgcta tagtaaccac gacgcggtgc
31981 aatcgtggtg accttctatt ttcaaatttt aaacacgcct caaacctcgt ccgaaaagtt
32041 tgaaactccc ccgagacatc cctttacac ccttgaacat gaatcaactc aaaaatctac
```

FIG. 6

```
31081 gctaagacca ccaagtcatt caaacaattc aagaggatgt gcatatcgaa attcatgaaa
31141 acttgtgcaa agattctctc ttgcaattca caaacatgtc gtggtcaagt atcttgtaac
31201 aaaccatgca actctctaaa atcatcacct ctcatttata taaacaagaa aacaccctct
31261 cttcacttca taaccaaaat caagtcttaa ataatagtaa agacattgat atcatgcttc
31321 tcaatatgca aattgaatat ttcataacct atgaaaacaa gatgctttat aacaagagag
31381 ggttatatat gttcatgctc tcaattcaat cattcaaact caaacgcatg tatacttaca
31441 tacgagtacg aatcaaattt aggggaaagc ctcaagacca aaatattata tcattgaaag
31501 agttcacact gcatgctttt taatgaaatt caagaaccct tcgtaaaaat atgatttctc
31561 gacattcaaa atatatttaa aatgatttta ccatgcccat gtagtttagg aaaacccaac
31621 gtaccttaga ttacttggtt cgaagaatag aattcgaatc ttgactcgtc tcttggaaat
31681 cttgaactta aagatggatt cttgatcttt tgggagggaa cttgatgtat <ttdggcatattatgcctt> aaagacgttt
31741 taatcttccg ttttcactac ttgggaccat ggaaaaaaga tgagactgcc cctcaacttt
31801 ttaaaaaatt actgcagaat ctccttttg gagctcactg cgacgcagtg acatgctcat
31861 tgccataccc accgcgacac ggtgtaatcg cggtgagtta ttgaaacttg accactgtcg
31921 atttgaattt caccgagacg cgacagaggc tccatcgcta tagtaaccac gacgcggtgc
31981 aatcgtggtg accttctatt ttcaaatttt aaacacgcct caaacctcgt ccgaaaagtt
32041 tgaaactccc ccgagacatc ccttttacac ccttgaacat gaatcaactc aaaaatctac
```

FIG. 7

SEQUENCE LISTING

<160> NUMBER OF SEQ ID NOS: 9

<210> SEQ ID NO 1
<211> LENGTH: 1020
<212> TYPE: DNA
<213> ORGANISM: Capsicum annuum

<400> SEQUENCE: 1

```
gctaagacca ccaagtcatt caaacaattc aagaggatgt gcatatcgaa attcatgaaa       60
acttgtgcaa agattctctc ttgcaattca caaacatgtc gtggtcaagt atcttgtaac      120
```

```
aaaccatgca actctctaaa atcatcacct ctcatttata taaacaagaa acaccctct    180 cttcacttca taaccaaaat caagtcttaa ataatagtaa agacattgat atcatgcttc   240
tcaatatgca aattgaatat ttcataacct atgaaaacaa gatgctttat aacaagagag   300
ggttatatat gttcatgctc tcaattcaat cattcaaact caaacgcatg tatacttaca   360
tacgagtacg aatcaaattt aggggaaagc ctcaagacca aaatattata tcattgaaag   420
agttcacact gcatgctttt taatgaaatt caagaaccct tcgtaaaaat atgatttctc   480
gacattcaaa atatatttaa aatgatttta ccatgcccat gtagtttagg aaaacccaac   540
gtaccttaga ttacttggtt cgaagaatag aattcgaatc ttgactcgtc tcttggaaat   600
cttgaactta aagatggatt cttgatcttt tgggagggaa cttgatgtat aaagacgttt   660
taatcttccg ttttcactac ttgggaccat ggaaaaaaga tgagactgcc cctcaacttt   720
ttaaaaaatt actgcagaat ctcctttttg gagctcactg cgacgcagtg acatgctcat   780
tgccataccc accgcgacac ggtgtaatcg cggtgagtta ttgaaacttg accactgtcg   840
atttgaattt caccgagacg cgacagaggc tccatcgcta tagtaaccac gacgcggtgc   900
aatcgtggtg accttctatt ttcaaatttt aaacacgcct caaacctcgt ccgaaaagtt   960
tgaaactccc ccgagacatc ccttttacac ccttgaacat gaatcaactc aaaaatctac  1020

<210> SEQ ID NO 2
<211> LENGTH: 18
<212> TYPE: DNA
<213> ORGANISM: Capsicum annuum

<400> SEQUENCE: 2
ttgggcatat tatgcctt                                                 18

<210> SEQ ID NO 3
<211> LENGTH: 23
<212> TYPE: DNA
<213> ORGANISM: Artificial sequence
<220> FEATURE:
<223> OTHER INFORMATION: Synthetic primer

<400> SEQUENCE: 3
ccctctcttc acttcataac caa                                           23

<210> SEQ ID NO 4
<211> LENGTH: 20
<212> TYPE: DNA
<213> ORGANISM: Artificial sequence
<220> FEATURE:
<223> OTHER INFORMATION: Synthetic primer

<400> SEQUENCE: 4
cggtgaaatt caaatcgaca                                               20

<210> SEQ ID NO 5
<211> LENGTH: 681
<212> TYPE: DNA
<213> ORGANISM: Capsicum annuum

<400> SEQUENCE: 5
ccctctcttc acttcataac caaaatcaag tcttaaataa tagtaaagac attgatatca    60
tgcttctcaa tatgcaaatt gaatatttca taacctatga aaacaagatg ctttataaca   120
agagagggtt atatatgttc atgctctcaa ttcatcatt caaactcaaa cgcatgtata   180
cttacatacg agtacgaatc aaatttaggg gaaagcctca agaccaaaat attatatcat   240
```

```
tgaaagagtt cacactgcat gcttttaat gaaattcaag aacccttcgt aaaaatatga      300
tttctcgaca ttcaaaatat atttaaaatg attttaccat gcccatgtag tttaggaaaa      360
cccaacgtac cttagattac ttggttcgaa gaatagaatt cgaatcttga ctcgtctctt      420
ggaaatcttg aacttaaaga tggattcttg atcttttggg agggaacttg atgtataaag      480
acgttttaat cttccgtttt cactacttgg gaccatggaa aaagatgag actgcccctc       540 aacttttaa aaaattactg cagaatctcc tttttggagc tcactgcgac gcagtgacat       600
gctcattgcc atacccaccg cgacacggtg taatcgcggt gagttattga aacttgacca      660
ctgtcgattt gaatttcacc g                                                681
```

```
<210> SEQ ID NO 6
<211> LENGTH: 699
<212> TYPE: DNA
<213> ORGANISM: Capsicum annuum

<400> SEQUENCE: 6
ccctctcttc acttcataac caaaatcaag tcttaaataa tagtaaagac attgatatca      60
tgcttctcaa tatgcaaatt gaatatttca taacctatga aaacaagatg ctttataaca     120
agagagggtt atatatgttc atgctctcaa ttcaatcatt caaactcaaa cgcatgtata    180
cttacatacg agtacgaatc aaatttaggg gaaagcctca agaccaaaat attatatcat    240
tgaaagagtt cacactgcat gcttttaat gaaattcaag aacccttcgt aaaaatatga     300
tttctcgaca ttcaaaatat atttaaaatg attttaccat gcccatgtag tttaggaaaa    360
cccaacgtac cttagattac ttggttcgaa gaatagaatt cgaatcttga ctcgtctctt    420
ggaaatcttg aacttaaaga tggattcttg atcttttggg agggaacttg atgtatttgg    480 gcatatatg ccttaaagac gttttaatct tccgttttca ctacttggga ccatggaaaa     540
aagatgagac tgcccctcaa cttttaaaa aattactgca gaatctcctt tttggagctc     600
actgcgacgc agtgacatgc tcattgccat acccaccgcg acacggtgta atcgcggtga    660
gttattgaaa cttgaccact gtcgatttga atttcaccg                           699
```

```
<210> SEQ ID NO 7
<211> LENGTH: 23
<212> TYPE: DNA
<213> ORGANISM: Artificial sequence
<220> FEATURE:
<223> OTHER INFORMATION: Synthetic primer

<400> SEQUENCE: 7
cataatatgc ccaaattcat caa                                              23
```

```
<210> SEQ ID NO 8
<211> LENGTH: 15
<212> TYPE: DNA
<213> ORGANISM: Artificial Sequence
<220> FEATURE:
<223> OTHER INFORMATION: Synthetic primer

<400> SEQUENCE: 8
ataatatgcc caaat                                                       15
```

```
<210> SEQ ID NO 9
<211> LENGTH: 21
<212> TYPE: DNA
<213> ORGANISM: Artificial sequence
<220> FEATURE:
```

```
<223> OTHER INFORMATION: Synthetic primer
<220> FEATURE:
<221> NAME/KEY: misc_feature
<222> LOCATION: (11)..(11)
<223> OTHER INFORMATION: w = a or t

<400> SEQUENCE: 9
aacgtctttt wcatcaagtt c                                              21
```

COMPOSITIONS AND METHODS FOR ASSAYING MARKERS TIGHTLY LINKED TO RESISTANCE LOCUS BS2 OF PEPPER

This application claims priority to U.S. Provisional Application No. 61/093,011, filed on Aug. 29, 2008, which is incorporated herein by reference in its entirety.

INCORPORATION-BY-REFERENCE OF SEQUENCE LISTING IN COMPUTER READABLE FORM

The Sequence Listing, which is a part of the present disclosure, includes a computer readable form 4.77 kb file entitled "MONS207US_seq_ST25.TXT" comprising nucleotide and/or amino acid sequences of the present invention submitted via EFS-Web. The subject matter of the Sequence Listing is incorporated herein by reference in its entirety.

FIELD OF THE INVENTION

The invention relates to identification of molecular markers tightly linked to the Bs2 resistance locus conferring resistance to Bacterial Spot, and methods for producing pepper plants resistant to *Xanthomonas campestris*.

BACKGROUND OF THE INVENTION

Peppers belong to the genus *Capsicum*, of the nightshade family, Solanaceae (e.g., *Capsicum annuum*). The term "pepper" may refer to the plant as well as its fruit. Peppers are commonly broken down into three groupings: bell peppers, sweet peppers, and hot peppers. Most popular pepper varieties fall into one of these categories, or as a cross between them. However, these groupings are not absolute, as both "hot pepper" and "sweet pepper" encompass members belonging to several different species. Additionally, members of each of the groups may be different cultivars of the same species. For example, the bell pepper, the jalapeno pepper, and the "Thai sweet" all belong to the species *Capsicum annuum* L. Hot peppers, including some inedible varieties, are grown for edible as well as ornamental and medicinal uses. While there are pungent (i.e., "hot") varieties of *C. annuum*, many well known hot peppers are members of different species. For example, both the cayenne pepper and the tabasco pepper are varieties of *Capsicum frutescens*, while the hottest peppers, including the habanero and naga varieties, are members of *Capsicum chinense*.

Pepper breeding efforts have focused in part on growing pepper plants resistant to diseases such as Bacterial Spot (BS), caused by the bacterium *Xanthomonas campestris* ("Xa"), including *X. campestris* pv. *vesicatoria* ("Xcv"). Bacterial Spot is one of the most important diseases of *Capsicum* sp. and causes necrotic spots on leaves, as well as premature leaf drop leading to sunscald of fruit, and spotting of stems and pods that results in unmarketable fruit. Leaf symptoms appear first on the undersides of leaves as small water-soaked areas. These spots may enlarge, turn dark brown, and are slightly raised. On the upper leaf surface the spots are depressed with a brown border around a beige center. Several lesions may coalesce, resulting in large necrotic areas, and large numbers of lesions can occur on leaf margins and tips where moisture accumulates. The disease is found worldwide and especially affects plants growing under warm moist conditions. Several classically defined resistance loci are known, including the resistance gene "Bs2", originating from *Capsicum chacoense* accession PI 260435, which provides resistance to *X. campestris* races 0, 1, 2, 3, 7, and 8, i.e., those races of the pathogen that contain the avirulence gene avrBs2.

Disease management and prevention requires use of pathogen-free seed, crop rotation, and/or spraying with antibacterial agents such as streptomycin and copper-containing compounds. Because the disease can spread rapidly under optimum conditions and greatly affect the yield and marketability of a pepper crop, the development of new pepper varieties having resistance to Bacterial Spot, and for rapid and efficient methods for identifying Bacterial Spot-resistant pepper plants, would represent a significant advance.

SUMMARY OF THE INVENTION

In one aspect, the invention provides a method for determining the genotype of a pepper plant for Bacterial Spot resistance, comprising obtaining a sample of nucleic acids from the plant and detecting in the nucleic acids a polymorphism at the Bs2_5859 locus that is genetically linked to Bacterial Spot Resistance. In certain embodiments, the step of detecting comprises PCR and/or DNA hybridization. In one embodiment, determining the genotype comprises a co-dominant assay. The polymorphism may comprise at least one of: a single nucleotide polymorphism (SNP) at a position corresponding to nucleotide 219, 237, 242, 269, 293, 351, 357, 359, 363, 369, 379, 413, 442, 443, 445, 461, 468, 470, 481, 535, 538, 548, 549, 557, 576, 585, 587, 648, 654, 669, 691, 693, 700, 716, 717, 742, 758, 761, 766, 796, 799, 801, 802, 804, 805, 811, 815, 822, 826, 829, 838, 847, 851, 852, 853, or 855 of SEQ ID NO:1, or a polymorphism in the number of nucleotides present between nucleotides 650 and 651 of SEQ ID NO:1.

In particular embodiments, the polymorphism comprises at least one of: a single nucleotide polymorphism (SNP) at a position corresponding to nucleotide 359, 468, 481, 538, 648, 716, or 717 of SEQ ID NO:1, or a polymorphism in the number of nucleotides present between nucleotides 650 and 651 of SEQ ID NO:1. In yet other particular embodiments, the polymorphism comprises a polymorphism in the number of nucleotides present between nucleotides 650 and 651 of SEQ ID NO:1.

In further embodiments, the polymorphism is detected by a screening method comprising use of at least a first sequence selected from the group consisting of SEQ ID NO:2, SEQ ID NO:3, SEQ ID NO:4, SEQ ID NO:7, SEQ ID NO:8, and SEQ ID NO:9. The method may, in specific embodiments, further comprises assaying the phenotype of a pepper plant for Bacterial Spot resistance.

In another aspect, the invention provides a method of producing a pepper plant having Bs2-mediated resistance to Bacterial Spot comprising the steps of: (a) crossing a pepper plant having Bs2-mediated resistance with a second pepper plant; and (b) selecting at least a first progeny pepper plant comprising a polymorphism at the Bs2_5859 locus that is genetically linked to resistance to Bacterial Spot. In certain embodiments, the step of selecting comprises PCR and/or DNA hybridization. In the method, the Bs2_5859 allele may be detected by a screening method comprising use of an oligonucleotide comprising a sequence selected from the group consisting of: SEQ ID NO:2, SEQ ID NO:3, SEQ ID NO:4, SEQ ID NO:7, SEQ ID NO:8, and SEQ ID NO:9. In one embodiment, the oligonucleotide consists of a sequence selected from the group consisting of: SEQ ID NO:2, SEQ ID NO:3, SEQ ID NO:4, SEQ ID NO:7, SEQ ID NO:8, and SEQ ID NO:9. In another embodiment, the screening method comprises detecting a co-dominant genetic marker. In still another embodiment, selecting the first progeny further comprises selecting the progeny based on the presence of one or more genetic markers from the second pepper plant genetically linked to at least a first additional trait. In a further embodiment of the method, the additional trait is selected from the group consisting of: yield, disease resistance, emergence vigor, vegetative vigor, stress tolerance, plant height, fruit quality, fruit diameter, fruit weight, fruit size, fruit length, fruit shape, fruit "hotness," fruit color, pungency, pericarp thickness, pedicel diameter, number of locules per fruit, number of days to flowering, and number of days to first ripened fruit.

In particular embodiments of the invention, a polymorphism is detected comprising at least one of: a single nucleotide polymorphism (SNP) at a position corresponding to nucleotide 219, 237, 242, 269, 293, 351, 357, 359, 363, 369, 379, 413, 442, 443, 445, 461, 468, 470, 481, 535, 538, 548, 549, 557, 576, 585, 587, 648, 654, 669, 691, 693, 700, 716, 717, 742, 758, 761, 766, 796, 799, 801, 802, 804, 805, 811, 815, 822, 826, 829, 838, 847, 851, 852, 853, or 855 of SEQ ID NO:1, or a polymorphism in the number of nucleotides present between nucleotides 650 and 651 of SEQ ID NO:1. In a further embodiment, a method of producing a pepper plant having Bs2-mediated resistance to Bacterial Spot as provided by the invention, further comprises the step of (c) crossing the progeny plant with itself or a third plant to produce a progeny plant of a subsequent generation and may further comprise the steps of: (d) crossing the progeny plant of a subsequent generation with itself or a second plant; and (e) repeating steps (c) and (d) for an additional 3-10 generations to produce an inbred pepper plant comprising Bacterial Spot resistance, wherein the progeny plant of at least one subsequent generation is screened for the presence of a polymorphism at the Bs2__5859 locus genetically linked to resistance to Bacterial Spot. In the method, the progeny plant of a subsequent generation may be selected for crossing based on the presence of resistance to Bacterial Spot and a desired trait. In one embodiment, the progeny plant of a subsequent generation is selected at each generation for crossing based on the presence of the resistance to Bacterial Spot and the desired trait. Selecting the progeny plant of a subsequent generation may further comprise selecting the progeny based on the presence of one or more genetic markers from the second pepper plant genetically linked to the desired trait. In the method, step (e) may be repeated with sufficient inbreeding to obtain an inbred pepper plant that comprises the resistance to Bacterial Spot and otherwise comprises the agronomic traits of the second pepper plant.

In yet another aspect, the invention provides a plant produced by a method of the invention. The invention also provides seed produced by a method of the invention, and the seed of a plant provided herein.

In still yet another aspect, the invention provides a method comprising recording on a computer readable medium the genotype of a plant or population of plants for at least a first polymorphism detected in accordance with the invention. The invention also provides a computer readable medium containing such information.

In still yet another aspect, the invention provides a method of producing peppers comprising: (a) obtaining a plant by a method of the invention; and (b) collecting peppers produced by the plant.

In still yet another aspect, the invention provides an isolated nucleic acid comprising a sequence of at least 18 contiguous nucleotides of SEQ ID NO:6, wherein the sequence is not present within SEQ ID NO:5. The invention also provides an isolated nucleic acid comprising a sequence selected from the group consisting of SEQ ID NO:2, SEQ ID NO:3, SEQ ID NO:4, SEQ ID NO:7, SEQ ID NO:8, and SEQ ID NO:9. Still further provided by the invention is an isolated primer or probe that amplifies and/or hybridizes to at least one polymorphism at a position corresponding to nucleotide 219, 237, 242, 269, 293, 351, 357, 359, 363, 369, 379, 413, 442, 443, 445, 461, 468, 470, 481, 535, 538, 548, 549, 557, 576, 585, 587, 648, 654, 669, 691, 693, 700, 716, 717, 742, 758, 761, 766, 796, 799, 801, 802, 804, 805, 811, 815, 822, 826, 829, 838, 847, 851, 852, 853, or 855 of SEQ ID NO:1, or that amplifies and/or hybridizes to a polymorphism present between positions corresponding to nucleotides 650 and 651 of SEQ ID NO:1, wherein the nucleotide sequence of the primer or probe is not comprised within SEQ ID NO:5.

BRIEF DESCRIPTION OF THE DRAWINGS

FIG. 1: Classification of races of *Xanthomonas campestris* pv. *vesicatoria* (Xa) pathogenic on pepper plants. Races of the pathogen are defined by the presence of avirulence genes specifying differential pathogenicity reactions on a panel of pepper lines.

FIG. 5: Sequence of a nucleic acid fragment from YAC AY702979, derived from a line harboring the Bs2 resistance locus, selected for primer design (SEQ ID NO:1). The underlined sequence illustrates primer locations for primers PB00058 (SEQ ID NO:3) and PB00059 (SEQ ID NO:4). The Bs2__5859 amplicon in resistant peppers (SEQ ID NO:5) includes bases 31255-31935 as numbered in FIG. 5.

FIG. 6: Bs2 5859 Amplicon sequence fragment from Xcv susceptible pepper line, shown with SNPs underlined. Fragment in brackets < > corresponds to indel polymorphism (insertion) present in susceptible lines, but neither in resistant lines, nor in the GenBank sequence derived from a resistant line.

FIG. 7: Haplotypes at the Bs2__5859 locus that are associated with Bs2-mediated resistance or susceptibility.

BRIEF DESCRIPTION OF THE SEQUENCES

Figure 2:
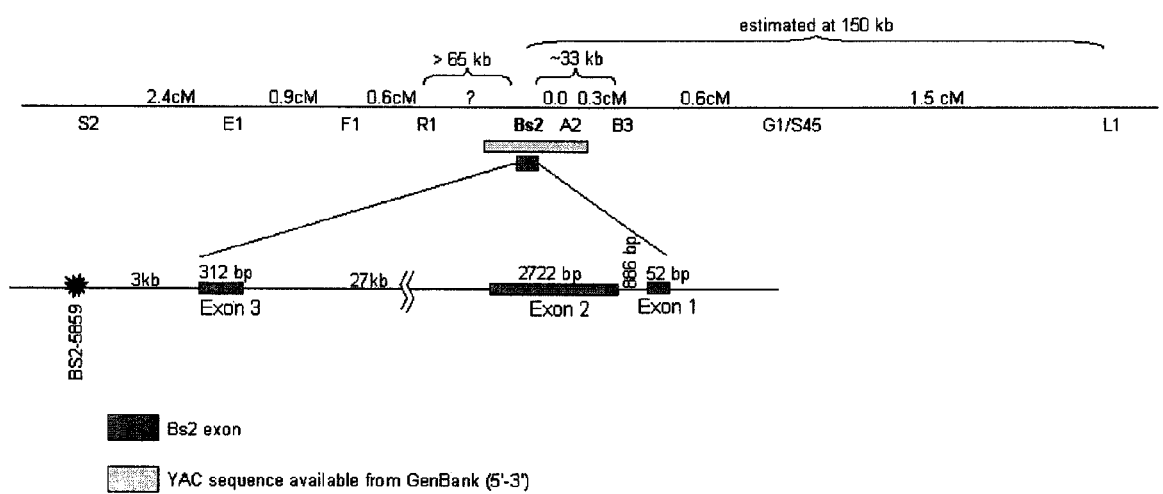
FIG. 2: Map showing location of the Bs2 resistance gene and other markers (adapted from Tai et al., 1999a, 1999b).

SEQ ID NO:1 Portion of YAC AY702979 including Bs2__5859 amplicon
SEQ ID NO:2 Indel identified in susceptible pepper lines
SEQ ID NO:3 Primer PB00058
SEQ ID NO:4 Primer PB00059
SEQ ID NO:5 Bs2__5859 amplicon from resistant pepper lines
SEQ ID NO:6 Bs2__5859 amplicon from susceptible pepper lines
SEQ ID NO:7 Primer PB00077

SEQ ID NO:8 TAQMAN® susceptible allele probe
SEQ ID NO:9 TAQMAN® resistant allele probe

DETAILED DESCRIPTION OF THE INVENTION

The present invention relates to identification of an amplifiable and assayable polymorphic locus closely linked to Bs2, a classically defined pepper disease resistance gene conferring resistance of plants to *X. campestris* races containing the avrBs2 avirulence gene. This polymorphic locus is termed the "Bs2__5859" or "5859" locus. One or more genetic marker(s) at this locus, such as DNA polymorphism(s), e.g., one or more single nucleotide polymorphism(s) (SNP) or an insertion/deletion ("Indel"), tightly linked to the 3' end of the Bs2 resistance gene, can thus be used as genetic marker(s) to detect the presence of the Bs2 resistance locus. The polymorphic locus may be defined as comprising an allele that is genetically linked to and identifies a phenotype of resistance to *X. campestris*, or an allele that is genetically linked to and identifies a susceptible phenotype. Thus, the invention provides specific molecular haplotypes at the Bs2__5859 locus that are associated with the presence or absence of a functional Bs2 resistance gene allele. In one embodiment, a Bs2 resistance sequence is represented in YAC clone YCA22D8 (U.S. Pat. No. 6,262,343; GenBank accession AY702979), from about by 34293 to about by 65288. Bs2 is a member of the nucleotide-binding site—leucine-rich repeat (NBS-LRR) polypeptide family, and many closely related family members are found in the pepper genome as well as in other Solanaceous plants. Successful use of an amplifiable marker within the Bs2 resistance gene itself has not been achieved, for instance due to a lack of specific amplification.

The 5859 locus was found to reside only about 3000 base pairs (bp) from the 3' end of the Bs2 coding sequence, and no recombination events were found between this marker and the resistance locus. The invention thus allows use of polymorphic sites at the 5859 locus to efficiently select for plants with resistance to *X. campestris* even under high selection pressure for other traits such as fruit quality, fruit diameter, fruit weight, fruit size, fruit length, fruit shape, fruit color, pungency, pericarp thickness, pedicel diameter, number of locules per fruit, and number of days to flowering, among others. The invention also provides PCR primers and reaction conditions whereby a marker, such as a deletion specific to peppers comprising the Bs2 resistance gene, can be detected in a dominant or co-dominant manner. Through use of the markers, one of skill in the art may select for Bacterial Spot resistance during breeding of a pepper line.

Previously described markers linked to the Bs2 resistance gene fail to provide an adequate selection tool because, for instance, the previously described markers are too distant from the Bs2 gene, and recombination events may occur which render them ineffective for selection purposes, or because the markers are based on a dominant assay wherein multiple PCR products are produced. Such dominant assays often can not be utilized in a high-throughput co-dominant SNP assay due to the complexity of the sequences in the vicinity of the Bs2 resistance locus.

FIG. 2 gives a schematic map of the pepper chromosome in the vicinity of the Bs2 locus, with genetic markers R1, F1, B3, A2, and S45, among others. In particular, regarding genetic markers in the vicinity of Bs2, use of primers corresponding to markers R1 and S45 did not result in reliable PCR amplification, with few lines, if any, yielding a detectable amplification product. Use of primers for A2 and F1 yielded 10 and 9 amplified SNP's, respectively. However, in contrast with Bs2__5859, none of these correlated with Bs2-mediated disease resistance. Use of primers at marker B3 identified 3 SNP's that matched the genotype at marker L1. However, these markers are not as closely genetically linked to Bs2 as is Bs2__5859, since linkage breaking lines are found (e.g., FIG. 3), with a susceptible phenotype but a "resistant" genotype.

Methods for detecting specific haplotypes at the Bs2__5859 locus, including appropriate PCR conditions and primers, are also provided. In certain embodiments the presence of a given haplotype at the Bs2__5859 locus is detected in a co-dominant assay.

In another aspect, the present invention provides a method of producing a Bacterial Spot resistant pepper plant comprising Bs2-mediated Xa resistance, wherein the method comprises: (a) crossing a pepper line having Bs2 resistance with a second pepper line lacking Bs2 resistance to form a segregating population; (b) screening the population for the presence of a polymorphism at the Bs2__5859 locus; and (c) selecting one or more members of the population having the Bs2__5859 polymorphism linked to Bs2 resistance.

In one aspect, the pepper line having Bs2 resistance is crossed with the second pepper line for at least two generations (e.g., creating either an $F_2$ or $BC_1S_1$ population). In another aspect, plants are identified as Xa resistant prior to crossing. In one aspect, plants can be selected on the basis of partial or complete resistance to Xa. In one aspect, the segregating population is self-crossed and the subsequent population is screened for resistance.

In another aspect, the present invention provides a method of introgres sing Bs2 resistance into a pepper plant comprising: (a) crossing at least a first pepper line having Bs2 resistance with a second pepper line to form a segregating population; and (b) selecting at least one member of the population exhibiting Xa resistance, wherein selection is based on the presence of a detectable haplotype at the Bs2__5859 locus. In one aspect, the pepper line having Bs2 resistance is crossed with the second pepper line for at least two generations (e.g., creating either an $F_2$ or $BC_1S_1$ population). In another aspect, plants are identified as Xa resistant prior to crossing. In one aspect, the segregating population is self-crossed and the subsequent population is screened for resistance.

As used herein, a "marker" is an indicator for the presence of at least one phenotype, genotype, or polymorphism. Markers include, but are not limited to, single nucleotide polymorphisms (SNPs), cleavable amplified polymorphic sequences (CAPS), amplified fragment length polymorphisms (AFLPs), restriction fragment length polymorphisms (RFLPs), simple sequence repeats (SSRs), insertion(s)/deletion(s) (INDEL(s)), inter-simple sequence repeats (ISSR), sequence characterized amplified region (SCAR) markers, and random amplified polymorphic DNA (RAPD) sequences. A marker may be inherited in co-dominant fashion (both alleles at a locus in a diploid heterozygote are readily detectable), with no environmental variance component, i.e., heritability of 1. A "nucleic acid marker" as used herein means a nucleic acid molecule that is capable of being a marker for detecting a polymorphism, phenotype, or both associated with Bacterial Spot resistance.

In one aspect of the invention, a plant is assayed for Bacterial Spot resistance, partial resistance or susceptibility to one or more race of *X. campestris* pv. *vesicatoria* (Xa). A chart classifying races of *X. campestris* pv. *vesicatoria*, the causal agent of Bacterial Spot of pepper, containing various combinations of avirulence genes, is found in FIG. 1. The type of resistance seen, for instance a hypersensitive response (HR) resistance reaction, or a non-hypersensitive resistance reaction, may be noted. In addition, the presence or absence of certain BS resistance genes may be noted by the disease profile of a certain pepper line across a panel of *Xanthomonas campestris* pv. *vesicatoria* races. For example, plants and progeny of ECW (Early Cal Wonder) pepper plants, and related near isogenic lines such as ECW 10R, ECW 20R, ECW 30R, and ECW 123, among others, may be subjected to phenotypic and genotypic tests to identify and correlate the presence of specific haplotypes at the Bs2__5859 locus with susceptibility or resistance to Xa. Additional pepper lines may include but are not limited to X3R Aladdin, X3R Camelot, X3R Candente, X3R Carmin, X3R Hot Spot, X3R Wizard, 27-1139, 99-1165, 99-1203, 99-1220, 99-1239, 99-1190, HP219, HP437, and lot 992946. Such work may aid in assay development and validation, and the identification of reaction conditions, including primer design, suitable for such tests. Use of a marker at the Bs2__5859 locus provides rapid and reliable molecular screening of candidate lines, and allows for genotypic screening of pepper breeding lines for Bs2-mediated resistance to *X. campestris* pv. *vesicatoria* without the necessity of a phenotypic disease assay.

One aspect of the present invention provides for a Bacterial Spot resistant pepper plant that comprises a genetic marker at the Bs2__5859 locus, linked to the Bs2 resistance locus. By "Bs2 resistance locus" is meant a locus that contributes to Bacterial Spot resistance either alone or in combination with one or more other Bacterial Spot resistance locus. By "contributes to Bacterial Spot resistance" it is meant that the degree of Bacterial Spot resistance is increased in the corresponding plant, either when the locus is alone or in combination with one or more other locus or loci. "Degree of Bacterial Spot Resistance" further may refer to either or both of qualitative and quantitative resistance, (e.g., HR- or non-HR-mediated resistance), including the number of races of Xa against which resistance is displayed.

Pepper lines having Bs2 resistance, or partial resistance, demonstrate a reduced level of symptoms relative to a non-resistant control pepper line after inoculation or infection with Xa. The level of symptoms can be used as an indicator of resistance to Bacterial Spot. Disease symptoms measured can be any disease symptoms associated with Xa infection. Symptoms can be selected from the group consisting of necrosis, raised lesions, disfigured fruit, sunscald of fruit, watersoaked leaf spots, or combinations thereof, among others. In one aspect, a Bs2 resistant pepper line demonstrates a reduction of foliar symptoms of watersoaked and/or necrotic lesions, or fruit lesions, of at least, or greater than, 10%, 20%, 25%, 30%, 40%, 50%, 60%, 70%, 75%, 80%, 85%, 90%, 95%, or 98% relative to a non-resistant control pepper line. In other aspects, the leaves of a Bs2 resistant pepper plant demonstrate less than 15%, or less than 10%, or less than 5%, or less than 2% symptomatic area when exposed to Xa. In another aspect, the pepper plant belongs to a pepper variety or cultivar, and in another aspect, the pepper plant is an inbred pepper plant.

Pepper lines resistant to Xa which have the susceptible genotype at the L1 marker locus and a resistant genotype at the Bs2__5859 locus described herein are also provided. Bacterial Spot resistant pepper plants of the present invention bear a resistance locus termed "Bs2" conferring Bacterial Spot resistance that has been introduced into the pepper plants from a line designated PI 260435 comprising the disease resistance, due to the tight linkage between the Bs_2 5859 locus and the Bs2 resistance gene.

Bs2 resistant pepper plants of the present invention may exhibit an increase in fruit yield after inoculation or infection with Xa relative to a control pepper plant (non Bs2-mediated resistant) inoculated with Xa. In one aspect, the resistant pepper plants exhibit a 2%, 5%, 10%, 15%, 20% or more increase in fruit yield, based upon the total mass, number, or total volume of fruit, relative to a control pepper plant after one or more rounds of inoculation or infection with Xa.

The present invention provides for and includes pepper plants that exhibit resistance to one or more races of Xa. In some embodiments, the pepper plants of the present invention exhibit resistance to 1, 2, 3, 4, 5, 6, or more races of Xa.

The present invention provides for a seed of a pepper plant capable of producing a plant having Bs2 resistance. In one aspect, the pepper plant can be an open-pollinated variety, a hybrid parent inbred line, or a male sterile line. In another aspect, the invention provides seed of a pepper plant capable of producing a hybrid pepper plant having resistance to Xa.

Once Bacterial Spot resistant plants are produced, the plants themselves can be cultivated in accordance with conventional procedures. Bacterial Spot resistant progeny may be obtained through sexual reproduction. The seeds resulting from sexual reproduction can be recovered from the fruit of Bacterial Spot resistant plants and planted or otherwise grown as a means of propagation. Bacterial Spot resistant progeny may also be obtained from Bacterial Spot resistant plants through asexual reproduction. Protoplast or propagules (e.g., cuttings, scions or rootstocks) can be recovered from Bacterial Spot resistant plants or parts thereof and may be employed to propagate Bacterial Spot resistant plants.

The present invention also provides progeny of pepper plants having resistance to Bacterial Spot, produced by the presently described methods. As used herein, progeny include not only, without limitation, the products of any cross (be it a backcross or otherwise) between two plants, but all progeny whose pedigree traces back to the original cross. In one aspect of the present invention, the progeny contain about 50%, 25%, 12.5% or less nuclear DNA from a Bacterial Spot resistant pepper plant and expresses the genetic material that provides Bacterial Spot resistance.

As used herein, linkage of two nucleic acid sequences, including a nucleic acid marker sequence and a nucleic acid sequence of a genetic locus imparting a desired trait such as Bs2 resistance, may be genetic or physical or both. In one aspect of the invention, the nucleic acid marker and genetic locus conferring Bs2 resistance are genetically linked, for instance exhibiting a LOD score of greater than 2.0, as judged by interval mapping for the Bs2 resistance trait based on maximum likelihood methods described by Lander and Botstein, 1989, and implemented in the software package MAPMAKER (e.g., Lander et al., (1987); default parameters). In other embodiments, the marker and region conferring Bs2 resistance are genetically linked and exhibit a LOD score of greater than 3.0, or a LOD score of greater than 6.0, 9.0, 12.0, 15.0, or 18.0.

In another aspect, the nucleic acid molecule may be physically linked to a Bs2 Bacterial Spot resistance locus. In some aspects, the nucleic acid marker specifically hybridizes to a nucleic acid molecule having a sequence that is within about 3000 bp of a Bs2 Bacterial Spot resistance locus.

As used herein, two nucleic acid molecules are said to be capable of hybridizing to one another if the two molecules are capable of forming an anti-parallel, double-stranded nucleic acid structure. Conventional stringency conditions are described by Sambrook et al. (1989), and by Haymes et al. (1985). Departures from complete complementarity are therefore permissible, as long as such departures do not completely preclude the capacity of the molecules to form a double-stranded structure. Thus, in order for a nucleic acid molecule to serve as a primer or probe it need only be sufficiently complementary in sequence to be able to form a stable double-stranded structure under the particular solvent and salt concentrations employed.

Appropriate stringency conditions which promote DNA hybridization, for example, 6.0× sodium chloride/sodium citrate (SSC) at about 45° C., followed by a wash of 2.0×SSC at 50° C., are known to those skilled in the art or can be found in Ausubel et al. (1989), §6.3.1-6.3.6. In some embodiments, hybridization conditions can be high, moderate or low stringency conditions. Exemplary conditions include those using 50% formamide, 5.0×SSC, 1% SDS and incubation at 42° C. for 14 hours, followed by a wash using 0.2×SSC, 1% SDS and incubation at 65° C.

The specificity of hybridization can be affected by post-hybridization washes. For example, the salt concentration in the wash step can be selected from a low stringency of about 2.0×SSC at 50° C. to a moderate stringency of about 1.0×SSC at 50° C. to a high stringency of about 0.2×SSC at 50° C. In addition, the temperature in the wash step can be increased from low stringency conditions at room temperature, about 22° C., to moderate stringency conditions at about 50° C., to high stringency conditions at about 65° C. Both temperature and salt concentration may be varied, or either the temperature or the salt concentration may be held constant while the other variable is changed. In some aspects, the wash step can be performed for 5, 10, 15, 20, 25, 30, or more minutes. In another aspect, the wash step is performed for about 20 minutes. In yet another aspect, the wash step can be repeated 1, 2, 3, 4, or more times using the selected salt concentration, temperature, and time. In another aspect, the wash step is repeated twice.

A genetic marker profile of a plant may be predictive of the agronomic traits of a hybrid produced using that inbred. For example, if an inbred plant of known genetic marker profile and phenotype is crossed with a second inbred of known genetic marker profile and phenotype it is possible to predict the phenotype of the $F_1$ hybrid based on the combined genetic marker profiles of the parent inbreds. Methods for prediction of hybrid performance from genetic marker data are disclosed in U.S. Pat. No. 5,492,547, the disclosure of which is specifically incorporated herein by reference in its entirety. Such predictions may be made using any suitable genetic marker, for example, SSRs, INDELs, RFLPs, AFLPs, SNPs, ISSRs, or isozymes.

Additional markers, such as SSRs, AFLP markers, RFLP markers, RAPD markers, phenotypic markers, SNPs, SCAR markers, isozyme markers, or microarray transcription profiles that are genetically linked to or correlated with Bs2 resistance can be utilized. Methods to isolate such markers are known in the art. For example, locus-specific SSRs can be obtained by screening a genomic library for markers specific to sequences found on the genomic clone of GenBank sequence AY702979, sequencing of "positive" clones, designing primers which flank the repeats, and amplifying genomic DNA with these primers.

As used herein, the progeny include not only, without limitation, the products of any cross (be it a backcross or otherwise) between two plants, but all progeny whose pedigree traces back to the original cross. Specifically, without limitation, such progeny include plants that have 50%, 25%, 12.5% or less nuclear DNA derived from one of the two originally crossed plants. As used herein, a second plant is derived from a first plant if the second plant's pedigree includes the first plant.

The present invention provides a genetic complement of the pepper lines described herein. Further provided is a hybrid genetic complement, wherein the complement is formed by the combination of a haploid genetic complement from elite inbred pepper lines described herein and another haploid genetic complement. Means for determining such a genetic complement are well-known in the art.

As used herein, the phrase "genetic complement" means an aggregate of nucleotide sequences, the expression of which defines the phenotype of a plant, such as a *C. annum* pepper plant or a cell or tissue of that plant. By way of example, a pepper plant is genotyped to determine a representative sample of the inherited markers it possesses. Markers may be inherited in co-dominant fashion so that the presence of both alleles at a diploid locus is readily detectable, and they are free of environmental variation, i.e., their heritability is close to, or equal to, 1. This genotyping is preferably performed on at least one generation of the descendant plant for which the numerical value of the trait or traits of interest are also determined. The array of single locus genotypes is expressed as a profile of marker alleles, two at each locus for a diploid plant. The marker allelic composition of each locus can be either homozygous or heterozygous. Homozygosity is a condition where both alleles at a locus are characterized by the same conditions of the genome at a locus (e.g., the same nucleotide sequence). Heterozygosity refers to different conditions of the genome at a locus. Potentially any type of genetic marker could be used, for example, simple sequence repeats (SSRs), insertion/deletion polymorphism (INDEL), restriction fragment length polymorphisms (RFLPs), amplified fragment length polymorphisms (AFLPs), single nucleotide polymorphisms (SNPs), and isozymes.

Considerable genetic information can be obtained from a completely classified $F_2$ population using a co-dominant marker system (e.g., Mather, 1938). An $F_2$ population is the first generation of self or sib pollination after the hybrid seed is produced. Usually a single $F_1$ plant is self or sib pollinated to generate a population segregating for the nuclear-encoded genes in a Mendelian (1:2:1) fashion.

In contrast to the use of co-dominant markers, using dominant markers often requires progeny tests (e.g., $F_3$ or back cross self families) to identify heterozygous individuals. The information gathered can be equivalent to that obtained in a completely classified $F_2$ population. Marker-assisted selection can then be applied to subsequent progeny based on marker-trait map associations ($F_2$, $F_3$), where linkage has not been completely disassociated by recombination events (i.e., maximum disequilibrium).

Recombinant inbred lines (RILs) (genetically related lines; usually >$F_5$) can be used as a mapping population. RILs can be developed by selfing F2 plants, then selfing the resultant F3 plants, and repeating this generational selfing process, thereby increasing homozygosity. Information obtained from dominant markers can be maximized by using RILs because all loci are homozygous or nearly so. Under conditions of tight linkage (i.e., about <10% recombination), dominant and co-dominant markers evaluated in RIL populations provide more information per individual than either marker type in backcross populations (e.g., Reiter et al., 1992). However, as the distance between markers becomes larger (i.e., loci become more independent), the information in RIL populations decreases dramatically when compared to co-dominant markers.

Backcross populations can be utilized as mapping populations. A backcross population (BC) can be created by crossing an $F_1$ to one of its parents. Typically, backcross populations are created to recover the desirable traits (which may include most of the genes) from one of the recurrent parental (the parent that is employed in the backcrosses) while adding one or a few traits from the second parental, which is often referred to as the donor. A series of backcrosses to the recurrent parent can be made to recover most of the recurrent parent's desirable traits. Thus a population is created consisting of individuals nearly like the recurrent parent, wherein each individual carries varying amounts or a mosaic of genomic regions from the donor parent. Backcross populations can be useful for mapping dominant markers particularly if all loci in the recurrent parent are homozygous and the donor and recurrent parent have contrasting polymorphic marker alleles (Reiter et al., 1992).

Information obtained from backcross populations using either co-dominant or dominant markers is less than that obtained from completely classified $F_2$ populations because recombination events involving one, rather than two, gametes are sampled per plant. Backcross populations, however, are more informative (at low marker saturation) when compared to RILs as the distance between linked loci increases in RIL populations (i.e., about 15% recombination). Increased recombination can be beneficial for resolution of tight linkages, but may be undesirable in the construction of maps with low marker saturation.

Near-isogenic lines (NIL) created by many backcrosses to produce an array of individuals that are nearly identical in genetic composition except for the trait or genomic region under interrogation can be used as a mapping population. In mapping with NILs, only a portion of the loci are polymorphic between the parentals are expected to segregate in the highly homozygous NIL population. Those loci that are polymorphic in a NIL population, however, are likely to be linked to the trait of interest.

Pepper plants generated using a method of the present invention can be part of or generated from a breeding program. The choice of breeding method depends on the mode of plant reproduction, the heritability of the trait(s) being improved, and the type of cultivar used commercially (e.g., $F_1$ hybrid cultivar, pure line cultivar, etc). Selected, non-limiting approaches for breeding the plants of the present invention are set forth below. A breeding program can be enhanced using marker assisted selection of the progeny of any cross. It is further understood that any commercial and non-commercial cultivars can be utilized in a breeding program. Factors such as, for example, emergence vigor, vegetative vigor, stress tolerance, disease resistance, branching, flowering, days to first ripened fruit, plant height, fruit size, fruit quality, and/or fruit yield will generally dictate the choice. In certain embodiments, by "fruit shape" is meant the ratio of fruit length to fruit diameter.

For highly heritable traits, a choice of superior individual plants evaluated at a single location will be effective, whereas for traits with low heritability, selection should be based on statistical analyses (e.g., mean values) obtained from replicated evaluations of families of related plants. Popular selection methods commonly include pedigree selection, modified pedigree selection, mass selection, and recurrent selection. In a preferred embodiment a backcross or recurrent breeding program is undertaken.

The complexity of inheritance influences choice of the breeding method. Backcross breeding can be used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Breeding lines can be tested and compared to appropriate standards in environments representative of the commercial target area(s) for two or more generations. The best lines are candidates as parents for new commercial cultivars; those still deficient in traits may be used as parents for hybrids, or to produce new populations for further selection.

One method of identifying a superior plant is to observe its performance relative to other experimental plants and to a widely grown standard cultivar. If a single observation is inconclusive, replicated observations can provide a better estimate of its genetic worth. A breeder can select and cross two or more parental lines, followed by repeated self or sib pollinating and selection, producing many new genetic combinations.

The development of new pepper lines requires the development and selection of pepper varieties, the crossing of these varieties and selection of superior hybrid crosses. The hybrid seed can be produced by manual crosses between selected male-fertile parents or by using male sterility systems. Hybrids can be selected for certain single gene traits such as flower color, seed yield or herbicide resistance that indicate that the seed is truly a hybrid. Additional data on parental lines, as well as the phenotype of the hybrid, influence the breeder's decision whether to continue with the specific hybrid cross.

Pedigree breeding and recurrent selection breeding methods can be used to develop cultivars from breeding populations. Breeding programs combine desirable traits from two or more cultivars or various broad-based sources into breeding pools from which cultivars are developed by selfing and selection of desired phenotypes into parent lines. These lines are used to produce new cultivars. New cultivars can be evaluated to determine which have commercial potential.

Pedigree breeding is used commonly for the improvement of self-pollinating crops. Two parents who possess favorable, complementary traits are crossed to produce an $F_1$. An $F_2$ population is produced by selfing one or several $F_1$'s. Selection of the best individuals in the best families is performed. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Backcross breeding and cross breeding have been used to transfer genes for a simply inherited, highly heritable trait into a desirable homozygous cultivar or inbred line, which is the recurrent parent. The source of the trait to be transferred is called the donor parent. The resulting plant obtained from a successful backcrossing program is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. After multiple backcrossing generations with selection, the resulting line is expected to have the attributes of the recurrent parent (e.g., cultivar) and the desirable trait transferred from the donor parent.

Cross breeding or backcross breeding of a Bacterial Spot resistant pepper plant may be conducted where the other parent (second pepper plant) is resistant to Xa or the other parent is not resistant to Xa.

Plants generated by the invention may be generated using a single-seed descent procedure. The single-seed descent procedure, in the strict sense, refers to planting a segregating population, then selecting one plant in this and each subsequent generation to self and create the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

Descriptions of other breeding methods that are commonly used for different traits and crops can be found in one of several reference books available (e.g., Fehr, 1987).

In another aspect, pepper lines having Bs2 resistance can be used in breeding programs to combine Bacterial Spot resistance with additional traits of interest. In one aspect, Bs2 resistance can be combined with any additional trait, including disease resistant traits, yield traits, and fruit quality traits. For example, breeding programs can be used to combine the Bs2 resistance trait with one or more other disease resistance traits, such as resistance to other races of Xa, *Phytophthora capsici*, Tobacco Mosaic Virus, or Cucumber Mosaic Virus, among others. In another aspect, the traits that are combined can be co-inherited in subsequent crosses.

The present invention also provides for parts of the Bs2-mediated Bacterial Spot resistant pepper plants produced by a method of the present invention. Parts of pepper plants, without limitation, include plant cells or parts of plant cells, seed, endosperm, meristem, flower, anther, ovule, pollen, fruit, flowers, stems, roots, stalks or leaves, scions, and root stocks. Plant parts also include the parts of a pepper fruit, which include the placenta, and pericarp. In one embodiment of the present invention, the plant part is a seed.

Those of skill in the art will appreciate the many advantages of the methods and compositions provided by the present invention. The following examples are included to demonstrate the preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention. All references cited herein are incorporated herein by reference to the extent that they supplement, explain, provide a background for, or teach methodology, techniques, or compositions employed herein.

Examples

Example 1

Comparison of Linkage Between Bs2, Bs25859, and L1; Identification of Lines Demonstrating Lack of Linkage Between Marker L1 and Bs2

Pepper line ECW 20R contains a functional Bs2 resistance allele, and displays hypersensitive resistance to Xa races 0, 1, 2, 3, 7, and 8. Pepper line ECW 10R does not contain the functional Bs2 resistance allele, and is susceptible to Xa races lacking the avrBs1 avirulence gene (e.g., FIG. 1). In ECW 20R, an introgression of *C. chacoense* sequence at the Bs2 locus conditions the resistance response, while ECW 10R lacks introgressed *C. chacoense*-derived sequences at and near this location.

Previously described genetic markers in the vicinity of Bs2, using primers corresponding to markers R1 and S45 (e.g., see FIG. 2) did not result in reliable PCR amplification, with few lines, if any, yielding a detectable amplification product. For instance, use of primers for A2 and F1 yielded 10 and 9 amplified SNP's, respectively. However, in contrast with Bs2__5859, none of these correlated with Bs2-mediated disease resistance. Use of primers at marker B3 identified 3 SNP's that matched the genotype at marker L1. However, these markers are not as closely linked, genetically, to Bs2 as is Bs2__5859, since linkage breaking lines are known (e.g., FIG. 3), with a susceptible phenotype but a "resistant" genotype.

Figure 3:
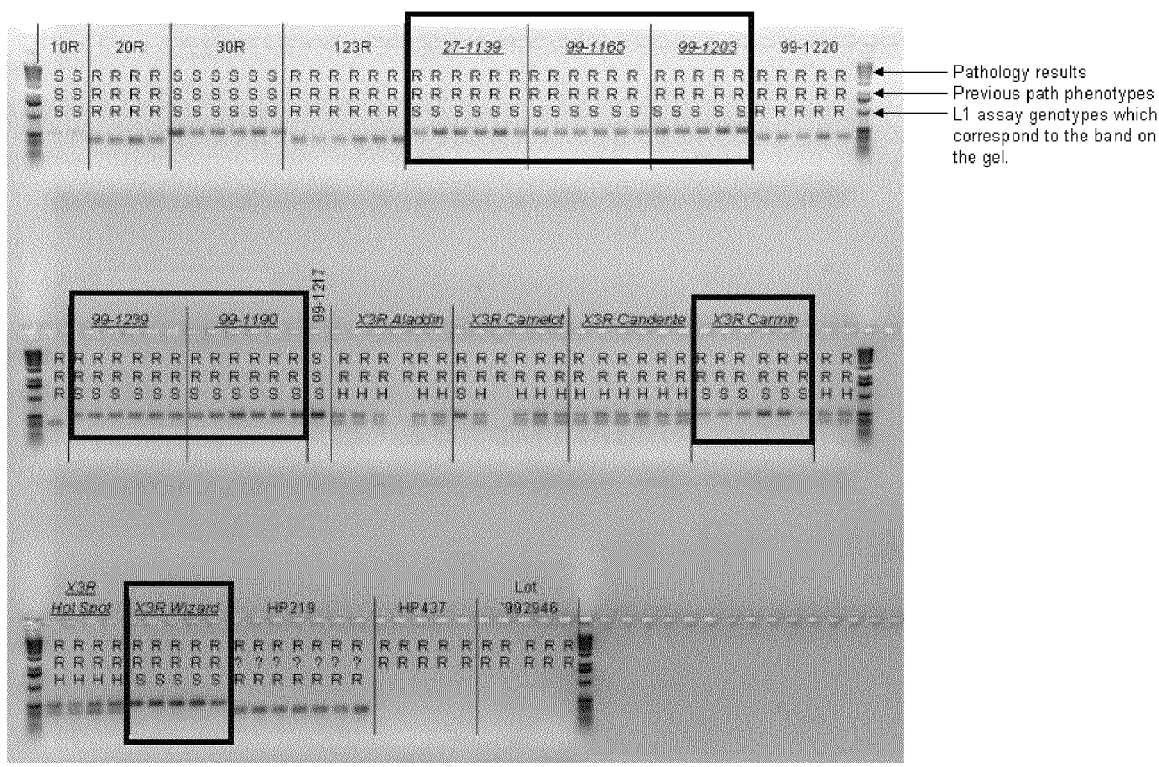
FIG. 3 Phenotypic and genotypic data showing linkage breaks between L1 and Bs2.

Plants derived from crosses between pepper lines with distinct levels of Bs2-mediated resistance were obtained, and certain resulting lines were genotyped at the 5859 locus and at nearby regions in their genomes flanking Bs2, Bs2__5859, and other genetically linked markers such as L1, and subjected to phenotypic tests for Xa resistance. Resistant lines displaying breakage of linkage between the Bs2 locus and marker L1 were identified. Exemplary genotypic data is shown in FIG. 3. Since the physical distance between L1 and the 5' end of Bs2 is approximately 150 kb, the breakage of linkage between these loci was not surprising. However, as shown in FIG. 2, the physical distance between the 3' end of Bs2 and the Bs2__5859 locus is only about 3 kb, and no breakage of linkage between specific Bs2__5859 haplotypes associated with Bs2-mediated disease resistance and the functional Bs2 resistance allele was observed in any tested line. This demonstrates the utility of use of markers at this location, Bs2__5859. Results of Bs2__5859 genotypic assays carried out as described in Example 5 showed that lines including 99-1165, 99-1217, 27-1139, 99-1203, 99-1239, and 99-1190 were linkage breaking lines (i.e., between L1 and Bs2).

Example 2

Characterization of Sequences Near the Bs2 Resistance Locus

Figure 4:
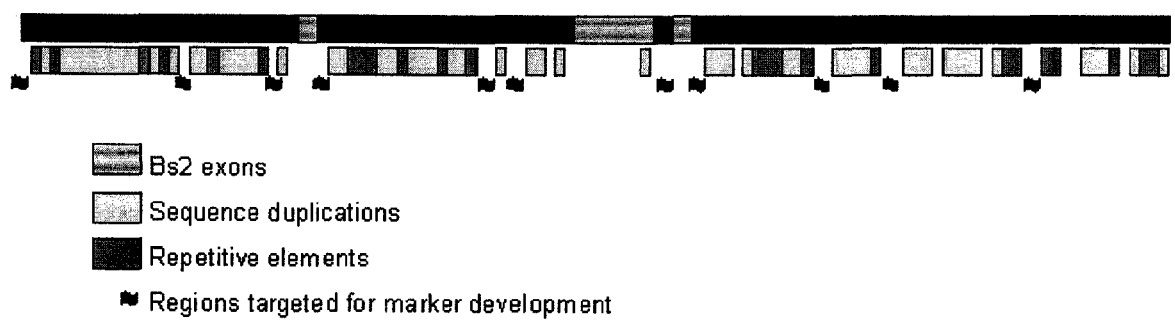
FIG. 4: Characterization of YAC sequences and targeted regions for marker identification, including sequences avoided for marker design, i.e., sequences identified and eliminated from consideration. AY702979 is a yeast artificial chromosome (YAC), approximately 103 kb in length, which contains the Bs2 resistance gene, shown in black; repetitive elements are shown in dark grey, and duplicated regions with greater than 70% similarity to another location within the YAC are shown in light grey. Bs2 exon sequence was also not targeted for marker design as it is known to be a member of a duplicated class of genes.

A yeast artificial chromosome (YAC) clone designated as YCA22D8 (GenBank AY702979) was found to include the region coding for the Bs2 resistance gene. This clone is approximately 103 kilobases (kb) in length. FIG. 2 is a schematic physical map of this clone, showing a number of existing markers in the vicinity of Bs2, such as S2, E1, F1, R1, A2, B3, G1/S45, and L1. FIG. 4 is a schematic diagram showing regions of the YAC sequence characterized as Bs2 exons, sequence duplications, repetitive elements, and regions targeted for marker development. This YAC clone contains numerous repetitive elements and duplicated sequences, both within and adjacent to the Bs2 sequence itself. The Blast2seq program (e.g., from the BLAST (Basic Local Alignment Search Tool) suite of NCBI, accessible on the world wide web at ncbi.nlm.nih.gov) was used to identify regions of the sequence that exhibited greater than 70% sequence similarity to other sequences on the YAC, in order to exclude such sequences from further analysis for marker development. The programs "Repeat grailexp" (e.g., Hyatt et al., 2000) and "Censor" (Jurka et al., 1996) were used to further analyze the YAC for repetitive elements. Twenty-two primer combinations were selected to amplify regions selected for marker development. However, a functional marker was not easily identified. Of those attempted amplifications, 10 gave PCR products with single bands appropriate for marker evaluation; the remaining 12 either yielded multiple bands or gave no amplification product. Of those 10, only 7 yielded sequence reliable enough to evaluate polymorphisms. Of those 7, 2 amplicons contained no polymorphisms, 4 amplicons contained polymorphisms that did not correlate with the Bs2 phenotype, and 1 amplicon, Bs2 5859, contained polymorphisms that correlated with the resistance trait and was designated marker Bs2_5859.

FIG. 5 illustrates a fragment of AY702979, designated Bs2 5859, corresponding to base pairs 31081-32100 of AY702979 (SEQ ID NO:1), which was selected for primer design and sequencing due to its lack of sequence duplication or the presence of repetitive elements (RE). The underlined sequence illustrates primer locations. Primer PB00058 (SEQ ID NO:3) comprises the sequence 5'-CCCTCTCTTCACT-TCATAACCAA-3'; bases 31255-31277 of AY702979; and primer PB00059 (SEQ ID NO:4) comprises the sequence 5'-CGGTGAAATTCAAATCGACA-3'; the complement of bases 31916-31935 of AY702979 as shown in FIG. 5. The italicized sequence of FIG. 5 (SEQ ID NO:5) represents the Bs2_5859 amplicon prepared from amplification of genomic DNA from a plant demonstrating Bs2-mediated Xa (e.g., Xcv) resistance.

Example 3

Identification of Bs2_5859 Polymorphisms

Sequencing of the Bs2_5859 amplicon yielded a sequence with numerous polymorphic sites that segregated with the trait of interest, i.e., Bs2-mediated Bacterial Spot resistance. SEQ ID NO:6, as shown within FIG. 6, represents the Bs2_5859 amplicon prepared from amplification of genomic DNA of Bs2 susceptible pepper plants, and shows the amplicon with indel (SEQ ID NO:2) associated with a susceptible phenotype. Additional polymorphic sites are underlined in FIG. 6. All unique haplotypes among phenotypically susceptible and resistant lines are displayed in FIG. 7. Lines which are listed as SBY99-1217, ECW10R, HP219, ECW30R, HJA114-1011, HSF111-1018, HSF114-1064 and HP235 are susceptible lines while samples ECW20R, 99-1220 and HP437 are derived from resistant lines. In the haplotype, only polymorphic sites are noted. Base pairs with a boxed outline have the same allele as resistant lines while the others illustrate those in susceptible lines. The grey base pairs show SNPs which are only present in susceptible lines and add to the complexity of the locus. Primary sequencing analysis of 12 pepper lines yielded 26 SNPs and one Indel at the Bs2_5859 locus. Further sequencing of lines as well as additional susceptible controls was conducted and a marker validation panel with additional polymorphisms was constructed. In total 57 lines were sequenced, and each line had 2-4 representatives.

Example 4

Assay Design and PCR Conditions

Figure 8:
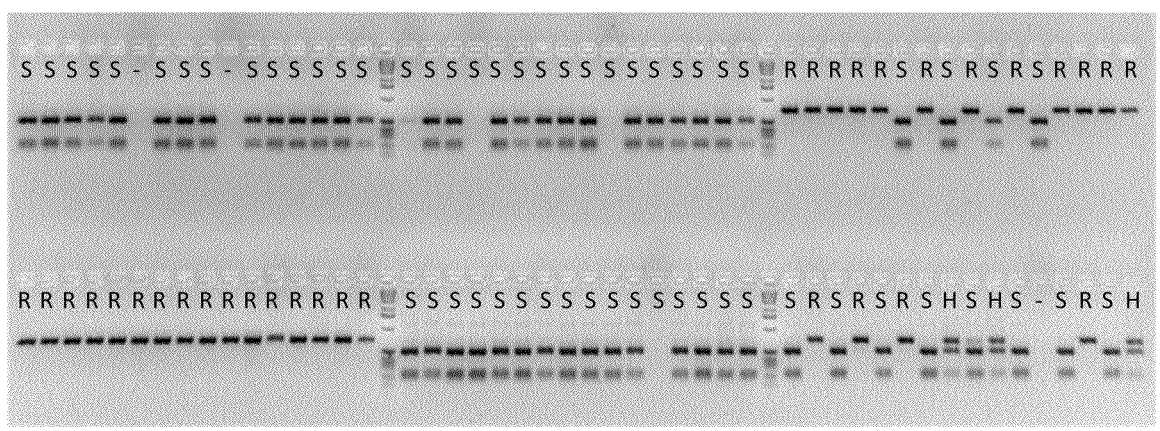
FIG. 8: Results of an exemplary co-dominant PCR-based marker assay at the Bs2__5859 locus. "S"=susceptible phenotype; "R"=resistant phenotype.

New assays were designed to overcome problems associated with previous markers linked to the Bs2 resistance gene. The previous markers which derived from AFLP's linked to Bs2 which do not yield usable assays included: A2, B3, F1, S45, and R1, as shown in FIG. 2, among others. An 18 by indel was found, the insertion correlating with susceptibility, and is tightly linked with the trait. This location of the indel was also used for additional primer design: primer PB00077 (SEQ ID NO:7: 5'-CATAATATGCCCAAATTCATCAA-3') corresponds to the reverse complement of a portion of the indel region shown in FIG. 6 and flanking sequence, and comprises bases not located in the YAC AY702979 sequence since the line used for cloning of the YAC is a Bs2 resistant line, which lacks the insertion that is present in susceptible lines. FIG. 2 further illustrates the relative physical locations of the Bs2 resistance gene, the previously described L1 marker, and the Bs2_5859 amplicon. FIG. 8 illustrates exemplary high throughput assay results.

Exemplary PCR conditions were defined as follows:

TABLE 1

PCR reaction conditions.

| Component | μl per reaction |
| --- | --- |
| water | 2.0 |
| USB 2X buffer | 7.5 |
| Primer PB00058 @ 5 μM | 1.0 |
| Primer PB00059 @ 5 μM | 1.0 |
| Primer PB00077 @ 5 μM | 1.5 |
| Template DNA | 2 |
| total | 15.0 |

The temperature profile used for the thermocycler was:
1. 94° C. 5 min.
2. 94° C. 30 sec
3. 50° C. 30 sec
4. 72° C. 1.5 min.
5. Repeat steps 2-4 for total of 33 cycles
6. 72° C. 7 min.
7. 25° C. hold A GENEAMP® PCR system 9700 and both the 96-well and dual 384-well, Applied Biosystems, Foster City, Calif. was used for the amplifications.

Example 5

Validation and Modification of a Bs2_5859 Assay

A validation panel was constructed without phenotypic knowledge prior to genotypic analysis. For instance, using the PCR protocol illustrated in Table 1, haplotypes were defined and a subset of corresponding sequences in selected lines were sequenced to confirm the predicted genotype. For this assay it was not possible to distinguish between heterozygotes and homozygous susceptible lines. In order to create an assay for use in high through-put marker assisted selection, modifications were made to the PCR conditions to create a co-dominant assay, thus separating out the three phenotypes of homozygous resistant, homozygous susceptible, and heterozygous. Under these modified conditions, PCR results of the homozygous susceptible genotypes often displayed a faint 700 by band, so band intensity may be a factor when distinguishing heterozygotes from homozygous susceptible plants. The assay was performed, for instance in a 384 well PCR plate, with the same PCR thermocycler program as the previous temperature profile, but with 35 cycles instead of 33 cycles being used.

TABLE 2

Modified PCR conditions.

| Component | μl per reaction |
| --- | --- |
| water | 1.486 |
| USB 2X buffer | 3.5 |
| Primer PB00058 @ 100 μM | 0.035 |

TABLE 2-continued

Modified PCR conditions.

| Component | μl per reaction |
|---|---|
| Primer PB00059 @ 100 μM | 0.035 |
| Primer PB00077 @ 100 μM | 0.07 |
| Template DNA | 2 |
| total | 7.126 |

Figure 7:
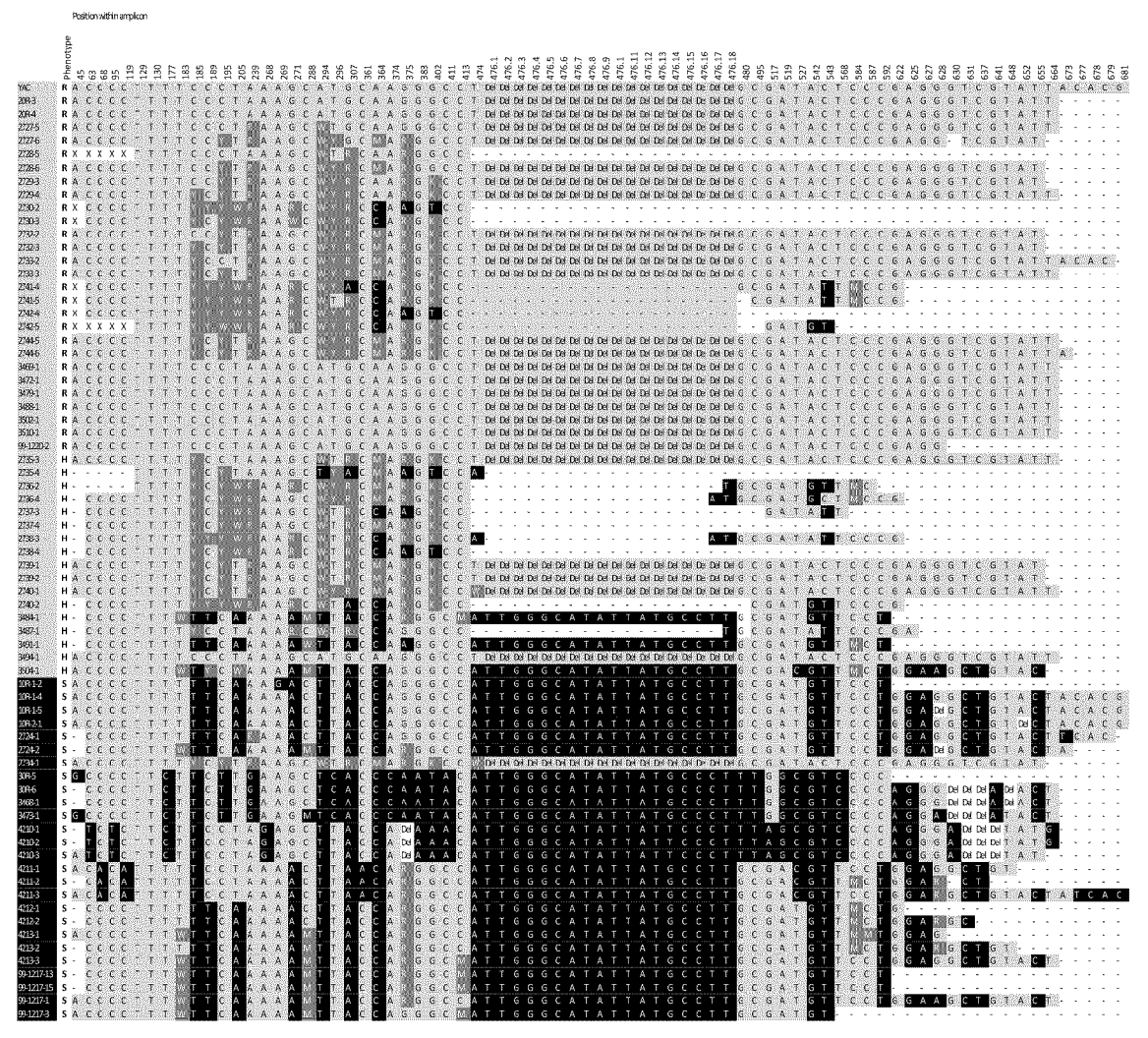

Amplification reactions for sequences at the Bs2_5859 locus were carried out on multiple pepper lines, and polymorphisms were seen at the locus in many lines (FIG. 7).

Example 6

Development of a High-Throughput Co-Dominant Assay at the Bs2_5859 Locus

Initially, custom TAQMAN® allele specific probes were designed to target the 18 bp indel of Bs2_5859. The susceptible allele probe (SEQ ID NO:8; 5'-ATAATATGCCCAAAT-3') which targeted the insertion was labeled with 6-carboxyfluorescein (6FAM). The resistance allele probe which spans the deletion (SEQ ID NO:9; 5'-AACGTCTTTTWCAT-CAAGTTC-3') was conversely labeled with VIC. Both probes were ordered and manufactured through Applied Biosystems. However, to improve the assay and provide an accurately predictive genotype, an additional assay was designed. In particular, to produce a co-dominant assay for Bs2_5859, restriction enzyme digests were investigated at various polymorphic sites throughout the amplicon, and specifically at the site of the 18 bp indel. To validate the assay's predictive capacity, lines exhibiting resistant, susceptible and segregating phenotypes in several breeding programs were collected and tested in the assay. The amplification and digestion conditions that were used are provided in Table 3 and Table 4:

TABLE 3

Additional PCR conditions.

| Component | 1X |
|---|---|
| water | 1.430 |
| USB 2X | 3.500 |
| Primer PB00058 @ 100 μm | 0.035 |
| Primer PB00059 @ 100 μm | 0.035 |
| DNA | 2.000 |
| Total rxn | 7.000 |

TABLE 4

Digest conditions.

| Digest | 1X |
|---|---|
| NEB 10X #3 | 1 |
| MwoI | 0.001 |
| water | 1.999 |
| total | 3 |

DNA was amplified using PB00058 and PB00059 (SEQ ID NOs:3-4) with the thermocycler temperature profile listed below. The digestion was set up and run overnight at 60° C.
1. 94° 5 min
2. 94° 30 sec
3. 50° 30 sec
4. 72° 1.5 min
5. Go to step 2-29 more times
6. 72° 7 min
7. 25° hold Three hundred lines have been validated to date and the assay has been 100% predictive for lines carrying the Bs2 resistance gene.

REFERENCES

The following references, to the extent that they provide exemplary procedural or other details supplementary to those set forth herein, are specifically incorporated herein by reference:

U.S. Pat. No. 5,492,547; U.S. Pat. No. 6,262,343.
Ausubel et al., *Current Protocols in Molecular Biology*, John Wiley & Sons, N.Y., 1989.
Fehr, *Principles of Cultivar Development* Vol. 1, pp. 2-3, 1987.
Haymes et al., *Nucleic Acid Hybridization, A Practical Approach*, IRL Press, Washington, D.C., 1985.
Hyatt, et al., *The 13th Annual Cold Spring Harbor Meeting on Genome Sequencing & Biology*, May 2000.
Jurka et al., *Comp. Chem.* 20:119-121, 1996.
Lander et al., *Genomics* 1:174-181, 1987.
Lander and Botstein, *Genetics,* 121:185-199, 1989.
Mather, *Measurement of Linkage in Heredity*: Methuen and Co., 1938.
Reiter et al., *Proc. Natl. Acad. Sci. (U.S.A.)* 89:1477-1481, 1992.
Sambrook et al., *Molecular Cloning, A Laboratory Manual*, 2nd Ed., Cold Spring Harbor Press, Cold Spring Harbor, N.Y., 1989.
Tai, et al., *Theor. Appl. Genet.* 99: 1201-1206, 1999a.
Tai, et al., *Proc Natl Acad Sci (U.S.A.)* 96: 14153-158, 1999b.

What is claimed is:

1. A method for determining the genotype of a pepper plant for Bacterial Spot resistance, comprising obtaining a sample of nucleic acids from said plant and detecting in said nucleic acids a polymorphism at the Bs2__5859 locus that is genetically linked to Bacterial Spot Resistance.

2. The method of claim 1, wherein the step of detecting comprises PCR.

3. The method of claim 1, wherein determining the genotype comprises a co-dominant assay.

4. The method of claim 1, wherein the step of detecting comprises DNA hybridization.

5. The method of claim 1, wherein the polymorphism comprises at least one of: a single nucleotide polymorphism (SNP) at a position corresponding to nucleotide 219, 237, 242, 269, 293, 351, 357, 359, 363, 369, 379, 413, 442, 443, 445, 461, 468, 470, 481, 535, 538, 548, 549, 557, 576, 585, 587, 648, 654, 669, 691, 693, 700, 716, 717, 742, 758, 761, 766, 796, 799, 801, 802, 804, 805, 811, 815, 822, 826, 829, 838, 847, 851, 852, 853, or 855 of SEQ ID NO:1, or a polymorphism in the number of nucleotides present between nucleotides 650 and 651 of SEQ ID NO:1.

6. The method of claim 5, wherein the polymorphism comprises at least one of a single nucleotide polymorphism (SNP) at a position corresponding to nucleotide 359, 468, 481, 538, 648, 716, or 717 of SEQ ID NO:1, or a polymorphism in the number of nucleotides present between nucleotides 650 and 651 of SEQ ID NO:1.

7. The method of claim 5, wherein the polymorphism comprises a polymorphism in the number of nucleotides present between nucleotides 650 and 651 of SEQ ID NO:1.

8. The method of claim 1, wherein the polymorphism is detected by a screening method comprising the use of at least a first sequence selected from the group consisting of SEQ ID NO:2, SEQ ID NO:7, SEQ ID NO:8, and SEQ ID NO:9.

9. The method of claim 1, wherein the method further comprises assaying the phenotype of the pepper plant for Bacterial Spot resistance.

10. A method of producing a pepper plant having Bs2-mediated resistance to Bacterial Spot comprising the steps of:
(a) crossing a pepper plant having Bs2-mediated resistance with a second pepper plant;
(b) assaying at least a first progeny pepper plant for a polymorphism at the Bs2__5859 locus that is genetically linked to resistance to Bacterial Spot; and
(c) selecting the at least first progeny plant comprising the polymorphism genetically linked to resistance to Bacterial Spot.

11. The method of claim 10, wherein the step of selecting comprises PCR.

12. The method of claim 10, wherein the step of selecting comprises DNA hybridization.

13. The method of claim 10, wherein the Bs2__5859 allele is detected by a screening method comprising the use of an oligonucleotide comprising a sequence selected from the group consisting of: SEQ ID NO:2, SEQ ID NO:7, SEQ ID NO:8, and SEQ ID NO:9.

14. The method of claim 13, wherein the screening method comprises detecting a co-dominant genetic marker.

15. The method of claim 10, wherein selecting the first progeny further comprises selecting the progeny based on the presence of one or more genetic markers from the second pepper plant genetically linked to at least a first additional trait.

16. The method of claim 15, wherein the additional trait is selected from the group consisting of: yield, disease resistance, emergence vigor, vegetative vigor, stress tolerance, plant height, fruit quality, fruit diameter, fruit weight, fruit size, fruit length, fruit shape, fruit color, pungency, pericarp thickness, pedicel diameter, number of locules per fruit, number of days to flowering, and number of days to first ripened fruit.

17. The method of claim 10, wherein the polymorphism comprises at least one of: a single nucleotide polymorphism (SNP) at a position corresponding to nucleotide 219, 237, 242, 269, 293, 351, 357, 359, 363, 369, 379, 413, 442, 443, 445, 461, 468, 470, 481, 535, 538, 548, 549, 557, 576, 585, 587, 648, 654, 669, 691, 693, 700, 716, 717, 742, 758, 761, 766, 796, 799, 801, 802, 804, 805, 811, 815, 822, 826, 829, 838, 847, 851, 852, 853, or 855 of SEQ ID NO:1, or a polymorphism in the number of nucleotides present between nucleotides 650 and 651 of SEQ ID NO:1.

18. The method of claim 10, wherein the polymorphism comprises at least one of: a single nucleotide polymorphism (SNP) at a position corresponding to nucleotide 359, 468, 481, 538, 648, 716, or 717 of SEQ ID NO:1, or a polymorphism in the number of nucleotides present between nucleotides 650 and 651 of SEQ ID NO:1.

19. The method of claim 10, wherein the polymorphism comprises a polymorphism in the number of nucleotides present between nucleotides 650 and 651 of SEQ ID NO:1.

20. The method of claim 10, further comprising the step of:
(c) crossing the progeny plant with itself or a third plant to produce a progeny plant of a subsequent generation.

21. The method of claim 20, further comprising the steps of:
(d) crossing the progeny plant of a subsequent generation with itself or a second plant; and
(e) repeating steps (c) and (d) for an additional 3-10 generations to produce an inbred pepper plant comprising Bacterial Spot resistance, wherein the progeny plant of at least one subsequent generation is screened for the presence of a polymorphism at the Bs2__5859 locus genetically linked to resistance to Bacterial Spot.

22. The method of claim 21, wherein said progeny plant of a subsequent generation is selected for crossing based on the presence of resistance to Bacterial Spot and a desired trait.

23. The method of claim 22, wherein the progeny plant of a subsequent generation is selected at each generation for crossing based on the presence of the resistance to Bacterial Spot and the desired trait.

24. The method of claim 22, wherein selecting the progeny plant of a subsequent generation further comprises selecting the progeny based on the presence of one or more genetic markers from the second pepper plant genetically linked to the desired trait.

25. The method of claim 21, wherein step (e) is repeated with sufficient inbreeding to obtain an inbred pepper plant that comprises the resistance to Bacterial Spot and otherwise comprises the agronomic traits of the second pepper plant.

26. A plant produced by the method of claim 25, said plant comprising Bs2-mediated resistance to Bacterial Spot and otherwise comprising the agronomic traits of the second pepper plant, wherein the second pepper plant is an elite inbred *Capsicum annuum* pepper line.

27. A seed of the plant of claim 26.

28. The method of claim 1, further comprising the step of storing the result of the step of detecting the polymorphism on a computer readable medium.

29. A method of producing peppers comprising:
   (a) obtaining the plant of claim 26; and
   (b) collecting peppers produced by the plant.

30. The method of claim 1, wherein the polymorphism is detected by PCR using oligonucleotides comprising SEQ ID NO:3 and SEQ ID NO:4.

31. The method of claim 11, wherein the Bs2_5859 allele is detected by PCR using oligonucleotides comprising SEQ ID NO:3 and SEQ ID NO:4.

* * * * *